(12) United States Patent
Horlitz et al.

(10) Patent No.: US 8,980,552 B2
(45) Date of Patent: Mar. 17, 2015

(54) METHOD FOR ISOLATING NUCLEIC ACIDS

(75) Inventors: Martin Horlitz, Düsseldorf (DE); Markus Sprenger-Haussels, Mettmann (DE)

(73) Assignee: QIAGEN GmbH, Hilden (DE)

( * ) Notice: Subject to any disclaimer, the term of this patent is extended or adjusted under 35 U.S.C. 154(b) by 275 days.

(21) Appl. No.: 13/378,466

(22) PCT Filed: Jun. 21, 2010

(86) PCT No.: PCT/EP2010/003724
§ 371 (c)(1),
(2), (4) Date: Mar. 2, 2012

(87) PCT Pub. No.: WO2010/145843
PCT Pub. Date: Dec. 23, 2010

(65) Prior Publication Data
US 2012/0171675 A1    Jul. 5, 2012

(51) Int. Cl.
*C12Q 1/68* (2006.01)
*C07H 21/00* (2006.01)
*C12N 15/10* (2006.01)

(52) U.S. Cl.
CPC .................................. *C12N 15/1006* (2013.01)
USPC .......................... 435/6.1; 536/22.1; 536/25.4

(58) Field of Classification Search
CPC ...... C12Q 1/68; C12N 15/00; C12N 15/1003; C12N 15/1006
USPC .................. 435/6.1; 536/22.1, 25.4
See application file for complete search history.

(56) References Cited

U.S. PATENT DOCUMENTS

| | | | |
|---|---|---|---|
| 2005/0009045 A1 | 1/2005 | Greenfield et al. | 435/6 |
| 2005/0032105 A1 | 2/2005 | Bair et al. | 435/6 |
| 2005/0059024 A1* | 3/2005 | Conrad | 435/6 |
| 2007/0072229 A1 | 3/2007 | Bialozynski et al. | 435/6 |
| 2007/0202511 A1 | 8/2007 | Chen et al. | 435/6 |

FOREIGN PATENT DOCUMENTS

| | | |
|---|---|---|
| WO | 01/71732 A2 | 9/2001 |
| WO | 2004/108925 A1 | 12/2004 |
| WO | 2005/012523 A1 | 2/2005 |

OTHER PUBLICATIONS

Analysis of circulating microRNA biomarkers in plasma and serum using quantitative reverse transcription-PCR (qRT-PCR). Methods 50 :298 (Feb. 2010).*
Horlitz, Martin et al., "Efficient Recovery of Viral and Circulating Cell-Free DNA and RNA from Plasma and Serum: The New Large Volume QIAamp® Circulating Nucleic Acid Kit," QIAGEN, Feb. 2009.
"miRNeasy Mini Handbook, For purification of total RNA, including miRNA, from animal and human cells and tissues," QIAGEN, Oct. 2007.
"mirVana™ miRNA Isolation Kit," Applied Biosystems, Jun. 3, 2008.
"PAXgene® Blood miRNA Kit Handbook," PreAnalytiX GmbH, May 2009.
Horlitz, Martin et al., "Efficient Recovery of Viral and Circulating Cell-Free DNA and RNA from Plasma and Serum: The New Large Volume QIAamp® Circulating Nucleic Acid Kit," QIAGEN, Mar. 2009.
"QIAamp® Circulating Nucleic Acid Handbook," QIAGEN, May 2009.
"Isolation of circulating microRNA using the QIAamp® Circulating Nucleic Acid Kit," QIAGEN Supplementary Protocol, first published online on Jul. 2, 2009.

* cited by examiner

Primary Examiner — Ethan C Whisenant
(74) Attorney, Agent, or Firm — Seed IP Law Group PLLC

(57) ABSTRACT

The invention describes a method of and kits for isolating and/or purifying nucleic acids, more specifically short-chain nucleic acids such as miRNA, from a nucleic acid-containing starting material, characterized by the following method steps of:
(a) binding the nucleic acids to a nucleic acid-binding support material by contacting the starting material with said nucleic acid-binding support material in the presence of at least one chaotropic compound, at least two different detergents and at least one branched and/or unbranched alcohol, preferably isopropanol, with the concentration of said alcohol being 40% (v/v);
(b) optionally eluting the bound nucleic acids from the nucleic acid-binding support material.
The method of the invention is particularly suitable for purifying circulating, extracellular miRNA from blood.

36 Claims, 5 Drawing Sheets

METHOD FOR ISOLATING NUCLEIC ACIDS

The present invention relates to a method of isolating and/or purifying nucleic acids, more specifically extracellular nucleic acids such as, for example, miRNA, from nucleic acid-containing samples, in particular blood.

Nucleic acids such as DNA and RNA are normally isolated from plant, animal or human materials and also from cell cultures or virus cultures according to a uniform basic pattern: the nucleic acid-containing starting materials are first disrupted—partly by using protein-degrading enzymes. In subsequent steps, the individual components can be removed using a wide variety of methods. In addition, nucleic acids may be isolated from sample materials in which they are free, i.e. not contained in cells. For example, free nucleic acids may occur in artificial sample mixtures, but also in natural samples such as blood, for example. Such free circulating nucleic acids are also referred to as extracellular nucleic acids.

Isolating extracellular nucleic acids, in particular short-chain microRNAs (miRNAs), from body fluids such as blood, plasma, serum, CSF, or even urine is of particular interest, since said nucleic acids may serve as biomarkers for diagnosing cancer or other diseases. In addition, the study thereof is of scientific interest. However, the analysis of these nucleic acids requires efficient purification which is actually quite challenging.

Although it is possible to purify short RNAs from body fluids such as whole blood and also cell-free blood fractions (plasma or serum) by methods known in the prior art, this is done only with comparatively low yield. In addition, there is a lack of methods in order to purify in particular free circulating nucleic acids such as, for example, microRNAs (miRNAs) from plasma or serum in an efficient manner. Free circulating microRNAs or else fetal or placenta-specific nucleic acids from plasma or serum are, however, important biomarkers for molecular diagnostics, for example for diagnosing tumors or for pregnancy and noninvasive prenatal diagnostics.

There is therefore a need for improved methods of isolating short-chain nucleic acids such as miRNAs from body samples such as blood or plasma or serum, which contain very low concentrations of said nucleic acids which are often also very short (≤50 nt). In addition to an efficient purification, it should preferably also be possible to process large sample volumes. Such a method would make it possible to detect very low concentrations of nucleic acids such as miRNAs, which are released, for example, from a small piece of tumor tissue or from the placenta into the blood (or plasma) with high sensitivity.

It is therefore an object of the present invention to provide a method for isolating and/or purifying nucleic acids, which can be used for efficiently isolating in particular extracellular and also short-chain nucleic acids such as in particular miRNA from samples.

Said object is achieved herein by a method for isolating and/or purifying nucleic acids, in particular free circulating nucleic acids, from a nucleic acid-containing starting material, which method is characterized by the following steps:
 (a) binding the nucleic acids to a nucleic acid-binding support material by contacting the starting material with said nucleic acid-binding support material in the presence of at least one chaotropic compound, at least two different detergents and at least one branched and/or unbranched alcohol, preferably isopropanol, with the concentration of said alcohol being ≥40% (v/v);
 (b) optionally eluting the bound nucleic acids from the nucleic acid-binding support material.

Due to the optimized extraction chemistry according to the invention, nucleic acids, more specifically free circulating nucleic acids such as in particular short-chain RNAs and in particular microRNAs (miRNAs) are efficiently bound to the nucleic acid-binding support material. This is achieved by means of a high alcohol concentration of ≥40% (v/v) during binding with simultaneous presence of a chaotropic compound and at least two detergents. Under these conditions, the yield of short-chain nucleic acids, in particular miRNA, is markedly higher and thus more efficient than using a standard protocol according to the prior art. This advantageous increase in yield is made possible in particular also due to the use of two different detergents, which was surprising. Moreover, the use according to the invention of a combination of two detergents enables the sample fluid to pass over small-area nucleic acid binding supports such as, for example, membranes, preferably silica membranes, without blocking the latter. As a result, the method of the invention advantageously enables large sample volumes to be processed on a small-area membrane and consequently a high concentration effect with regard to the nucleic acids to be isolated to be achieved.

The support material may be selected from the group consisting of silica-containing materials, silicon dioxide gel, silicon dioxide, glass, zeolite, aluminum oxide, titanium dioxide, zirconium dioxide, kaolin, diatoms, silica gel or ceramic. The porous or nonporous support material may be present in bulk or in the form of filter layers or membranes.

According to a preferred embodiment, the nucleic acid-binding support material is therefore a nucleic acid-binding membrane or a nucleic acid-binding filter or a filter layer which preferably has fine pores. They may have any kind of shape and can thus be round or square, for example. According to one embodiment, the diameter of the membranes and/or filters or filter layers is ≤10 mm, preferably ≤7 mm. The surface is therefore as small as possible in order to be able to achieve a small elution volume. According to one embodiment, it is ≤80 mm$^2$, preferably ≤40 mm$^2$. In one embodiment, the membrane or filter/filter layer has a thickness in a range of 0.5-3 mm, preferably 0.7-1.3 mm. According to one embodiment, the mass per unit area is 50-400 g/m$^2$, preferably 100-180 g/m$^2$. Particle retention (i.e. the lower limit of permeability to particulate substances) is usually within a range of 0.05 μm-100 μm, preferably 0.1-20 μm. Using a corresponding silica membrane is particularly suitable.

The use of membranes or filters or filter layers, however, particularly has the problem of frequent blockage thereof at the high alcohol concentrations employed according to the invention, possibly due to unspecific precipitation of plasma components. As a result, using said high alcohol concentrations increases the yield of the desired short-chain nucleic acids but makes processing of the samples more difficult. In this context, the simultaneous presence of two detergents, preferably an ionic and a nonionic detergent, has surprisingly been found to allow solubilization of the precipitates and therefore also the vacuum- or centrifugation-based passing of large volumes of binding mixtures over a small-area membrane. This is a particular advantage when relatively large sample volumes (for example of at least 1 ml, preferably at least 3 ml or at least 4 ml) are processed. Sample volumes of this kind are usually required for isolating extracellular nucleic acids, for example when isolating the very short-chain miRNAs from plasma, since this nucleic acid species is present in the sample always at only very low concentrations. The method of the invention, however, advantageously enables large sample volumes to be processed effectively and with that the free circulating nucleic acids to be isolated effectively and with good yield, owing to the particular binding conditions.

Preferably, at least one ionic detergent is used in combination with at least one nonionic detergent. This combination has proved being advantageous. The ionic detergent is preferably used in an amount of at least ≥0.05% (w/v), with a range from 0.1 to 5% (w/v), preferably 0.1 to 2% (w/v), particularly preferably 0.1 to 0.2% (w/v) having proved particularly suitable. According to one embodiment, the nonionic detergent is used in higher amounts of at least ≥0.5% (w/v), preferably ≥1% (w/v), particularly preferably ≥4% (w/v). Concentrations in a range from at least 5 to 8% (w/v) have proved particularly suitable.

Ionic detergents in accordance with the present invention comprise anionic, cationic and zwitterionic detergents, with anionic detergents being particularly preferred. The detergents used according to the invention are preferably surfactants.

Preferred anionic detergents are sulfates, sulfonates, phosphates and carboxylic acids, which are preferably present as salt, for example as alkali metal salt or alkaline earth metal salts, for example as sodium, lithium or potassium salt, or as free acid. Anionic detergents may be in particular sulfates of fatty alcohols, in particular with an unbranched or branched alkyl chain of from 4 to 28 carbons, preferably 8 to 18 carbons, or alkylaryl sulfonates, in particular linear alkylbenzene sulfonates. Specific examples of anionic detergents are sodium dodecyl sulfate (SDS), lithium dodecyl sulfate, sodium octyl sulfate, sodium dodecyl sulfonate, sodium decyl sulfonate, sodium octyl sulfonate, dodecylbenzenesulfonic acid (DDBSA), N-lauroylsarcosine, sodium cholate, sodium deoxycholate. Examples of cationic detergents are in particular quaternary ammonium compounds such as cetyltrimethylammonium bromide (CTAB). Preferred zwitterionic detergents are 3-[(3-cholamidopropyl)dimethylammonio]-1-propane sulfonates (CHAPS) or related detergents.

Quaternary ammonium compounds having at least one long alkyl chain may be used as cationic detergents.

Nonionic detergents comprise polyoxyethylene detergents, in particular polyoxyethylene alkyl ethers, the alkyl part being preferably an unbranched or branched alkyl group of from 4 to 28, preferably 8 to 24, more preferably 12 to 20, carbon atoms and the polyoxyethylene part having at least 2, preferably at least 4, more preferably 6 to 24 ethylene units, polyoxyethylene alkylaryl ethers in which a phenyl group substituted with an alkyl group preferably in the para position is coupled to the polyoxyethylene group, and detergents of the Triton X series. Specific examples of suitable nonionic detergents are Brij 58, Brij 30, Brij 35, Brij 56, Brij 72, Brij 90, Igepal CA-630, Span 20, Span 60, Span 80, Tween 20, Tween 80, Triton X-100, Triton X-114, Triton X-450, digitonin and Nonidet P-40.

Suitable detergents for the present invention can also be found inter alia in the product catalogue of Sigma-Aldrich (Life Science, Biochemicals & Reagents).

A combination of Brij 58 and SDS has proved particularly suitable.

Preference is given to using short-chain branched or unbranched alkanols having from one to five carbon atoms such as, for example, methanol, ethanol, propanol, isopropanol, butanols or pentanols. It is also possible to use mixtures of the relevant alcohols. Particular preference is given to using isopropanol or an alcohol or alcohol mixture with isopropanol-like properties. The alcohol concentration during binding is ≥40% (v/v), preferably ≥42.5% (v/v). However, dependent on the alcohol, it is also possible to use higher alcohol concentrations of ≥50% or even ≥60%. The alcohol concentration is preferably ≤80% (v/v), particularly preferably ≤70% (v/v), however.

Suitable chaotropic compounds which promote binding of the free circulating nucleic acids to the support material may be selected based on the "Hofmeister series". According to the latter, strongly chaotropic anions are $NO_3^-$, $ClO_4^-$, $SCN^-$, $NCS^-$, and $Cl_3CCO^-$. Examples of strongly chaotropic cations are $Ba^{2+}$ and guanidinium. Chaotropic compounds that are preferably employed are thiocyanates, isothiocyanates and/or perchlorates, in particular guanidinium thiocyanate or guanidinium isothiocyanate. Further chaotropic agents which may be employed according to the invention are guanidinium hydrochloride, guanidinium carbonate, sodium iodide, sodium perchlorate, urea and thiourea. As described, it is also possible to use mixtures of multiple chaotropic agents.

Preference is given to employing the chaotropic compound in high concentrations. Said concentration is preferably at least ≥1 mol/l. Suitable ranges are therefore between ≥1 and ≤8 mol/l, preferably in a range from ≥1.3 to ≤5, ≥1.3 to ≤4, and particularly preferably in a range from ≥1.0 to ≤3 mol/l.

Various materials and in particular biological materials may be used as nucleic acid-containing starting materials. The term "starting material" comprises any nucleic acid-containing material and therefore both natural samples and prepared samples or sample components, and also artificial samples such as, for example, solutions containing nucleic acids (for example from a synthesis or PCR reaction). The method is particularly suitable for isolating/purifying free nucleic acids from samples that do not contain cells or appropriately prepared samples or sample components. A cell-free sample may be obtained by removing the cells by centrifugation, for example. The method of the invention is particularly suitable, for example, for isolating nucleic acids such as DNA and/or RNA from sample materials of human or animal origin, in particular from clinical samples such as blood, plasma, serum, mouth wash, urine, cerebral fluid, CSF, sputum, stool, aspirate, epithelial swabs, biopsies, and other tissues or bone marrow samples. The method of the invention is particularly suitable for isolating free circulating nucleic acids such as, for example, tumor DNA and tumor RNA, fetal nucleic acids and miRNAs from body fluids such as blood, in particular plasma and/or serum.

Nucleic acids which may be isolated by the present method are, for example, DNA, RNA, mRNA, mitochondrial, modified nucleic acids, for example epigenetically modified, single-stranded, double-stranded, circular, plasmid, cosmid, artificial or synthetic nucleic acids, and also cDNA and fragments thereof. The method of the invention is particularly suitable for concentrating short-chain nucleic acids (for example DNA and RNA in any form, including noncoding RNA such as, for example, miRNA or synthetic nucleic acids) of ≤1000 nt, ≤800 nt, ≤500 nt, ≤300 nt, ≤200 nt, ≤100 nt, or ≤50 nt in length. Preference is given to purifying DNA and/or RNA. DNA or RNA of ≤50 nucleotides in length can be purified particularly efficiently. Depending on the nucleic acid-containing starting material, the method of the invention produces normally a nucleic acid mixture which contains in particular also the short-chain nucleic acids. These may then be prepared further, for example processed, modified or analyzed. To isolate RNA, the purified nucleic acid is preferably treated with DNase. The RNA thus obtained also contains the short-chain RNA when the method of the invention is used.

The nucleic acids to be purified have preferably one or more of the following characteristics:

a) they are ≤500 nt, ≤400 nt and/or ≤300 nt and/or ≤100 nt and or ≤50 nt in length;

b) they are RNA and/or DNA;
c) they are extracellular nucleic acids;
d) they are non-protein-coding RNAs;
e) they are RNAi-inducing nucleic acids, more specifically siNAs.

The term "siNA" (short interfering nucleic acid) refers in particular to nucleic acids or functional variants or derivatives thereof which are capable of inducing RNAi (RNA interference) processes. They may be both single-stranded and double-stranded. According to one embodiment, the siNA is a double-stranded polynucleotide which has self-complementary sense and antisense strands. The term also encompasses precursors of corresponding double-stranded molecules. siNAs which may also be mentioned in particular are microRNAs (miRNAs). MicroRNAs have been found to be valuable both for scientific and for diagnostic purposes (utilization of miRNAs as biomarkers). MicroRNAs are short, highly conserved, noncoding RNA molecules which play an important part in the complex network of gene regulation, in particular in gene silencing (switching off genes). MicroRNAs regulate gene expression highly specifically at the post-transcription level. They were found to be present also free in body fluids such as blood in particular and may therefore be important diagnostic markers. Accordingly, there is a need for purifying miRNAs with great efficiency from body fluids such as blood in particular. However, miRNAs are generally less than 25 nt in size and are also present only in low concentrations, making their purification more difficult.

Since the samples contain always only low concentrations of the short-chain nucleic acids such as miRNA in particular, it is desirable to process a large sample volume. According to one embodiment, the volume of the nucleic acid-containing starting material is therefore ≥1 ml, preferably ≥3 ml.

To achieve a sufficient concentration of said nucleic acids, preference is also given to employing a small elution volume. The latter is preferably in a range from 10 to 200 µl, preferably 10 to 150 µl. This can be achieved in particular when using a small-area nucleic acid-binding membrane, preferably a silica membrane or a corresponding filter or filter layer.

The invention therefore provides an optimized protocol in particular for purifying short-chain nucleic acids, in particular extracellular nucleic acids and in particular miRNA, which protocol firstly allows a large sample volume to be processed in order to increase thereby the absolute yield of nucleic acids and in particular miRNA. For reasons of completeness, it should be noted that, in addition to the short-chain nucleic acids such as in particular the miRNAs, other nucleic acids (long- and short-chain) may also be copurified. This also depends on the kind of sample and the kind of nucleic acids present therein. Decisive is only that the purified sample contains a sufficient amount of the desired nucleic acids such as, in particular, short-chain nucleic acids such as miRNAs. If it is desired to specifically concentrate the relevant short-chain nucleic acids (for example in relation to long-chain nucleic acids), suitable preliminary steps may be carried out in order to first deplete relatively long-chain nucleic acids, for example. This may be achieved, for example, by adjusting the binding conditions, for example by using a lower alcohol concentration and/or a lower concentration of a chaotropic compound. Performing a DNase digestion is advantageous if RNA is to be specifically purified.

The method of the invention also allows a small elution volume to be utilized (ideally 20 to 50 µl) such that the eluate contains a high concentration of the nucleic acids. By employing a modified binding chemistry, the yield of very short nucleic acids of less than 50 nucleotides and preferably less than 25 nucleotides is markedly increased compared to the methods known in the prior art. The present invention therefore provides a valuable addition to the existing prior art methods for purifying relevant nucleic acids.

In certain cases, the sample may be used without pretreatment in the method of the invention. However, in many cases it may be necessary to firstly disrupt the sample by a suitable method and release the biological material contained in said sample. Methods for disrupting samples and cells are known to the skilled worker and may be of a chemical, enzymatic or physical kind. It is also possible to combine these methods.

In this context, different factors may prove to be advantageous for different biological materials; in principle, the following methods are well-suited: lysis with the aid of ionic and nonionic detergents such as, for example, SDS, LiDS or sarcosyl in suitable buffers, the use of chaotropic salts such as, for example, guanidinium hydrochloride (GHCL), guanidinium thiocyanate (GTC), guanidinium isothiocyanate (GITC), sodium iodide, sodium perchlorate, and others; mechanical tearing apart, for example by means of a French Press, ultrasound, grinding with glass beads, nickel beads, aluminum, or in liquid nitrogen; enzymatic lysis, for example with lysozyme, proteinases, proteinase K or cellulases, or by means of other commercially available enzymes for lysis; lysis of the cells by means of bacteriophages or viral infections; freeze-drying; osmotic shock; microwave treatment; temperature treatment; for example heating or boiling or freezing, for example in dry ice or liquid nitrogen, and thawing; alkaline lysis. As discussed, the above methods are state of the art with regard to lysis and are well known and therefore need not be explained in detail.

When purifying free circulating nucleic acids and in particular RNAi-inducing nucleic acids such as, for example, miRNAs, from a blood sample, first the cells and other solid components of the blood may be removed (for example by centrifugation), and the plasma thus obtained be processed further. Said plasma is usually free of cells but does contain the extracellular nucleic acids, for example fetal nucleic acids, tumor DNA and/or RNA, and miRNAs. The purification of free nucleic acids such as, for example, miRNA from plasma does not require actual cell lysis in order to release said nucleic acids because the latter are already in a free circulating form. This also applies to other samples which contain free nucleic acids that accordingly are not located inside cells. However, such extracellular, i.e. free circulating or free, nucleic acids may be associated with proteins and/or other substances. For this reason, the nucleic acid-containing starting material, for example blood plasma, is first treated with a release buffer which ensures that the nucleic acids are released from the associated form. Function and composition of the release buffer are similar to those of a lysis buffer which is employed for cell disruption. The release buffer generates in the sample suitable conditions for releasing the nucleic acids, which as a result are not present by way of a complex. Addition of the release buffer renders the nucleic acid more accessible to purification. The method of the invention may accordingly also be employed for cell-free starting materials. Depending on its composition, the corresponding release buffer may also work as lysis buffer. Normally, the usual lysis buffers may also be employed as release buffers. The terms are therefore also used synonymously herein.

According to the invention, the use of release or lysis buffers containing chaotropic agents is particularly effective, even more so since the composition of the release or lysis buffer also influences the conditions under which the nucleic acids bind to the support material. The binding conditions in the sample which are crucial according to the invention for the efficacy of the method of the invention, may therefore also be adjusted by choosing the release or lysis buffer in a suitable manner, for example in combination with a binding buffer. Release or lysis buffers according to the present invention contain a chaotropic compound such as, for example, GTC or GHCL, and optionally already the detergents employed according to the invention, such as SDS and Brij 58, for example. These agents may be present in aqueous solution or in a buffer solution, i.e. as "release buffer" or "lysis buffer". The buffer employed may be any suitable buffer such as, for example, Tris, Bicine, Tricine, or phosphate buffer. Alternatively, the lysis or release agent may also be added separately. Suitable concentrations and amounts of the lysis or release agents vary depending on the respective systems, kind of cells, etc. and may be determined by a person skilled in the art.

Chaotropic compounds are also present in the sample mixture during binding of the nucleic acids to the support material. Details of this have been explained in detail above. The chaotropic compounds may be, for example, derived from the lysis or release buffer and/or may be added separately, however, for example in the form of a binding buffer. Ultimately, the binding conditions in the sample during binding of the nucleic acids to the support material are decisive. Here, the chaotropic compound may be present ultimately up to the limit of solubility. The use of chaotropic compounds is advantageous for efficient binding of the nucleic acids and in particular of the short-chain nucleic acids.

The detergents may likewise either be added with the release/lysis buffer or else be part of the binding buffer, for example. A separate addition is also possible. Detergents cause efficient solubilization of various components in the sample, for example of serum and plasma components. This is particularly advantageous when a silica membrane is used. As has been demonstrated herein, the efficiency of the purification method of the invention was surprisingly markedly improved by employing at least two detergents, preferably an ionic and a nonionic detergent.

As discussed, it is possible to employ, for example, nucleic acid-binding filters or filter layers and membranes and in particular silica membranes. Liquids may be removed here by centrifugation or applying a vacuum or by pressure or gravity. In many applications of the method of the invention, in particular in the purification of nucleic acids from blood samples (preferably plasma or serum), the nucleic acids to be purified will be present at low concentrations in large volumes. The prior art use of a silica membrane often has the problem of a possible blockage of the membrane by large sample volumes. However, this problem does not occur according to the method of the invention. The method is therefore also less time-consuming and can also be carried out in an automated manner.

According to one embodiment, the nucleic acid-binding support material is a nucleic acid-binding solid phase from the group consisting of silica-containing materials, silicon dioxide gel, silicon dioxide, glass, zeolite, aluminum oxide, titanium dioxide, zirconium dioxide, kaolin, silica gel, ceramic, or polymeric support materials, and also polystyrene beads or coated magnetic or paramagnetic particles. Decisive is at the end that the support material is capable of binding nucleic acids. Particular preference is given to employing silica materials. Here, the use both of silica membranes or silica filters or filter layers and of magnetic (e.g. super-, para-, ferri- or ferromagnetic) particles having a silica or glass surface has proved to be worthwhile. Said particles may substantially be pearl-shaped or spherical and preferably have a particle size in the range of 0.02-30 µm, preferably 0.05-15 µm, and particularly preferably of 0.1-10 µm. Magnetic silica particles which may be employed advantageously in the method of the invention are described, for example, in the international application WO 01/71732, the entire contents of which are hereby incorporated by reference. As discussed, preference is given to employing a nucleic acid-binding membrane or a nucleic acid-binding filter.

Optionally, the method of the invention may comprise carrying out washing steps using wash buffers and/or wash solutions known in the prior art. According to one embodiment, the wash buffers contain chaotropic substances. Preferably, the wash buffers contain at least 40% (v/v), preferably at least 50% (v/v) of one or more alcohols in order to maintain binding of the short-chain nucleic acids to the solid phase and thus prevent the nucleic acids from being accidentally washed out of the support. Particular preference is given to a wash buffer containing chaotropic substances and at least 50% (v/v) of one or more alcohols.

The nucleic acids bound to the support material are then preferably removed from said support material, for example eluted in a manner known per se, if a recovery of the short-chain nucleic acids is desired. Suitable elution buffers and solutions are known in the prior art.

The nucleic acids isolated according to the invention may then be processed further in the known manner, i.e. analyzed, for example. However, depending on the planned subsequent further processing or analysis, it is likewise possible to employ the nucleic acids bound to the support material and thus without elution. The method may also be employed for removing nucleic acids from a sample.

The method of the invention is particularly suitable for use in diagnostics. The method of the invention may be carried out manually or else also in an automated manner and may therefore also be employed for application to appropriate purification robots. Further fields of application can be found, for example, in forensics and in other fields in which the purification of small nucleic acids such as, for example, miRNA is important.

The invention also specifically provides a method of isolating and/or concentrating RNAi-inducing nucleic acids, more specifically miRNAs, from a blood sample, more specifically from blood plasma, which method is characterized by the features described above. The suitable method conditions are described in detail above; reference is made to the disclosure above.

The invention also provides a kit for isolating and/or purifying nucleic acids, in particular short-chain nucleic acids, from a nucleic acid-containing starting material. Said kit comprises buffers and/or reagents for carrying out the method of the invention and also instructions for carrying out said method. A corresponding kit is particularly suitable for concentrating or purifying miRNAs from a blood sample.

BRIEF DESCRIPTION OF THE FIGURES

The accompanying drawings (FIGS. 1-3b), which are incorporated herein and form part of the specification, illustrate the results of exemplary experiments of the present disclosure.

EXAMPLES

Figure 1:
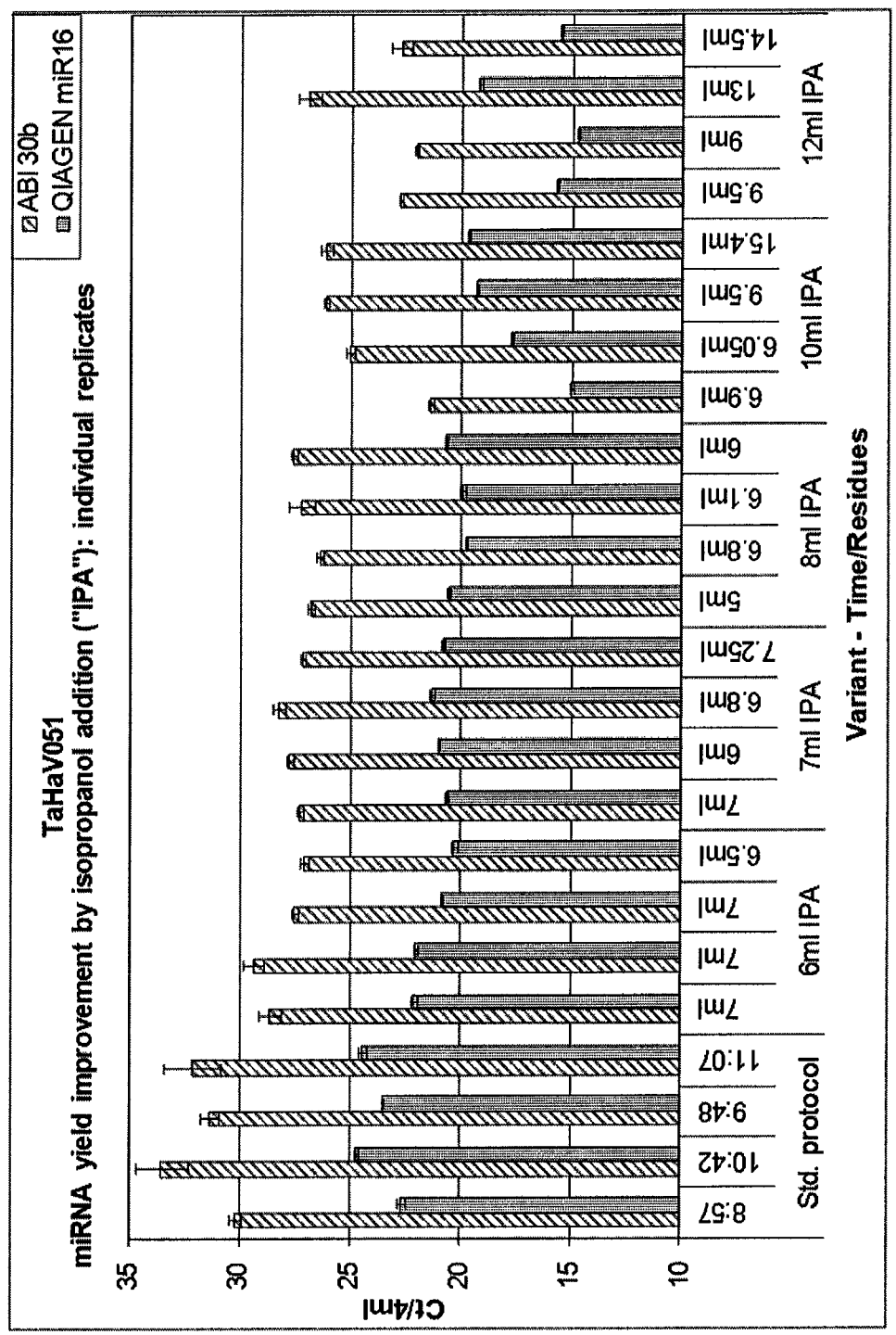
Figure 1:
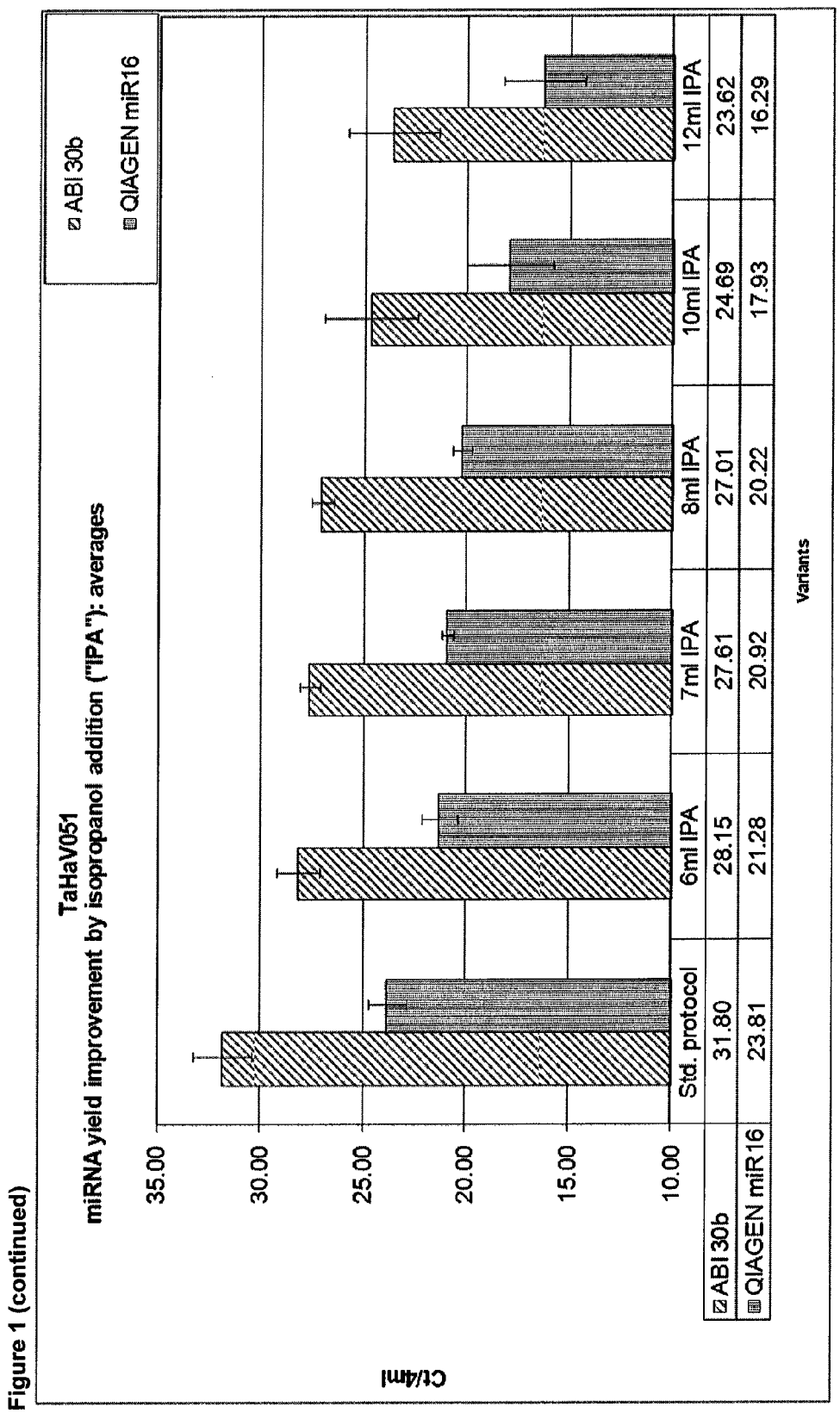

The present invention will now be illustrated on the basis of examples which represent preferred embodiments of the invention. The experiments performed were carried out on the basis of the experimental protocols described below.

The protocol according to the invention was compared to a standard protocol known in the prior art, namely the QIAamp Circulating Nucleic Acid Kit (QIAGEN cat. no. 55114). The QIAamp Circulating Nucleic Acid Kit is a manual procedure for extracting free circulating nucleic acids from plasma, serum and other cell-free body fluids. The sample is disrupted in the presence of chaotropic salt and a proteinase K, with subsequent binding of the nucleic acids to a silica membrane (QIAamp Mini Column) being mediated by a chaotropic salt and isopropanol (approx. 19-20% v/v). Under these conditions, even very short RNA molecules, for example microRNAs (20-22 nt in length) can be purified—but with a limited yield. The binding conditions of the abovementioned standard protocol are suboptimal for nucleic acids that short.

The abovementioned standard protocol was varied according to the invention by adding to the binding buffer in addition isopropanol and detergent for binding of the nucleic acids. The details regarding the concentrations of key components during binding of nucleic acids to the QIAamp Mini Column are listed in tables 1 to 3. The sample material used was a plasma mixture of multiple blood donors; the nucleic acid extraction was carried out following this protocol.

The following experiments were carried out according to the experimental protocol described:

I. Example 1

Disruption of the Sample

For this, 500 µl or 400 µl of QIAGEN proteinase K were pipetted into a 50 ml tube, and 5 ml or 4 ml of plasma were added. 3.2 ml of ACL buffer (QIAGEN, without addition of carrier RNA, contains inter alia a chaotropic agent, a nonionic detergent and Tris-HCl, pH 8.0) is added, the cap is sealed, followed by mixing by pulse vortexing for 30 s.

The sample was heated to 60° C. and incubated for 30 min. The tube was briefly spun in order to remove drops from the inside of the lid.

Binding

For this, 7.2 ml of buffer ACB (QIAGEN, contains inter alia a chaotropic agent, a nonionic detergent, isopropanol and Tris-HCl, pH 8.0) were added to the lysate (and in the case of the 4 ml samples 6 ml, 7 ml, 8 ml, 10 ml and 12 ml of isopropanol), the lid was closed, followed by thorough mixing by pulse vortexing for 15-30 s. The mixture is incubated on ice for 5 min.

A column (QIAamp Mini Column) was employed for purification. The column is placed in a vacuum pump, and a 20 ml extension tube is placed into the open column. The extension tube must be inserted tightly into the column in order to prevent a loss of the sample. The disrupted sample is introduced into the extension tube of the column and the vacuum pump is switched on. Once the complete lysate has been drawn through the column, the vacuum pump is switched off and the underpressure is reduced to 0 mbar. The extension tube is carefully removed.

DNase Digestion

The column is transferred to a 2 ml collecting tube and centrifuged at 14 000 rpm for 1 min. This step removes lysate residues which could possibly prevent DNase digestion. For each sample, 10 µl of DNase stock solution are added to 70 µl of buffer RDD (QIAGEN) and mixed by inverting the sample.

The columns are returned to their original positions. The DNase I incubation mix (80 µl) is applied to the silica gel membrane of the column and incubated at moderate temperatures (20-30° C.) for 15 min.

Washing

For washing, 600 µl of buffer ACW1 (QIAGEN, contains inter alia a chaotropic agent and ethanol) are applied to the column. The lid of the column is left open and the vacuum pump is switched on. After all of buffer ACW1 has passed through the column, the vacuum pump is switched off and the pressure is reduced to 0 mbar.

The column is charged with 750 µl of wash buffer ACW2 (QIAGEN, contains inter alia a chaotropic agent and salts). The lid of the column is left open and the vacuum pump is switched on. After all of buffer ACW2 has passed through the column, the vacuum pump is switched off and the pressure is reduced to 0 mbar.

After this 750 µl of ethanol (96-100%) are applied to the column. The lid of the column is left open and the vacuum pump is switched on. After all of the ethanol has passed through the column, the vacuum pump is switched off and the pressure is reduced to 0 mbar.

The lid of the column is closed, and the column is placed into a clean collecting tube. This is followed by centrifuging the column at full speed (20 000×g, 14 000 rpm) for 3 min.

Elution

The column is placed into a new 2 ml collecting tube, the lid is opened and the assembly is incubated at 56° C. for 10 min in order to dry the membrane completely.

The column is placed into a clean 1.5 ml elution tube and the collecting tube is removed. To the center of the membrane of the column, 20-150 µl of elution buffer (AVE buffer, QIAGEN) are applied. The lid is closed followed by incubation at room temperature for 3 min.

Centrifugation is carried out at full speed for 1 min (20 000×g; 14 000 rpm) in order to elute the nucleic acids. The eluate contains both circulating DNA and RNA.

Table 1 summarizes the binding conditions in example 1:

|  | Standard protocol | +6 ml IPA | +7 ml IPA | +8 ml IPA | +10 ml IPA | +12 ml IPA |
| --- | --- | --- | --- | --- | --- | --- |
| Gu thiocyanate | 2.3 mol/l | 1.6 mol/l | 1.6 mol/l | 1.5 mol/l | 1.4 mol/l | 1.3 mol/l |
| Isopropanol | 19.5% | 42.7% | 45.3% | 47.7% | 51.9% | 55.5% |
| Brij 58 | 10.2% | 7.2% | 6.9% | 6.6% | 6.1% | 5.6% |
| Total volume | 14.8 ml | 20.8 ml | 21.8 ml | 22.8 ml | 24.8 ml | 26.8 ml |
| Replicates: | 4 repl. | 4 repl. | 4 repl. | 4 repl. | 4 repl. | 4 repl. |

After analyzing the miRNA yield by means of reverse transcription/real time PCR assays, the following was obtained (see also FIG. 1). The Ct values (normalized to a uniform sample volume of 4 ml) for the miRNAs 16 and 30b indicate that the miRNA yield also increases with an increase in the isopropanol concentration during binding. Moreover, it became obvious already during the experimental procedure that it was possible only with the standard protocol to load the samples completely onto the QIAamp columns; in all the other cases, the columns were blocked to such an extent that the loading procedure had to be interrupted and remaining lysate had to be discarded. For the standard protocol, the flow-through times for the lysate are indicated. In all the other cases, the remaining lysate residual volumes are documented (FIG. 1, top graph).

Apparently, the increase in isopropanol concentration in the lysate results in effects which hamper the vacuum-based loading of the lysate onto the QIAamp column—possibly due to unspecific precipitation of plasma components which then by way of microparticles block the pores of the QIAamp membrane. This is a problem for a routine execution of the protocol.

At least it was possible for the addition of 12 ml of isopropanol (approx. 55.5% v/v in the binding mixture) to improve the miRNA yield by 7.5 to 8.2 Cts compared to the standard protocol—this corresponds to a 180- to 290-fold increase in yield. FIG. 1 shows the results.

II. Example 2

In a second experiment, the experimental conditions were modified as follows, owing to the results obtained in experiment 1:

For nucleic acid binding, isopropanol concentrations below 42% were also assayed.

The amount of binding buffer ACB was increased to 9 ml per sample

For "6 ml of isopropanol" and "12 ml of isopropanol", addition of a sodium dodecyl sulfate-containing buffer, for example ATL (QIAGEN, contains inter alia Tris, pH 7.5 to 8.5, and SDS), was also assayed (3 ml of sample and 1 ml of buffer ATL).

The protocol was therefore carried out as follows:

Disruption of the Sample

400 µl of QIAGEN proteinase K are pipetted into a 50 ml tube, and 4 ml [3 ml] of plasma are added. 3.2 ml of ACL buffer (QIAGEN, without carrier RNA) are added and, in the case of the 3 ml samples, additionally 1 ml of buffer ATL, the cap is sealed, followed by mixing by pulse vortexing for 30 s.

The sample is heated to 60° C. and incubated for 30 min. The tube is briefly spun in order to remove drops from the inside of the lid.

Binding

For this, 7.2 ml of ACB buffer (QIAGEN) were added to the lysate (and also 0 ml, 2 ml, 4 ml and 6 ml of isopropanol in the case of the 4 ml samples, and 6 ml or 12 ml in the case of the 3 ml samples), the lid was closed, followed by thorough mixing by pulse vortexing for 15-30 s. The mixture is incubated on ice for 5 min.

A column (QIAamp Mini Column) may be employed for purification. The column is placed in a VacConnector, and a 20 ml extension tube is placed into the open column. The extension tube must be inserted tightly into the column in order to prevent a loss of the sample. The disrupted sample is introduced into the extension tube of the column and the vacuum pump is switched on. Once the complete lysate has been drawn through the column, the vacuum pump is switched off and the underpressure is reduced to 0 mbar. The extension tube is carefully removed.

The remaining steps (washing and elution) were carried out as described in example 1.

The sample material used was a plasma mixture of various blood donors—but a different lot than that used in example 1. The concentrations of the important components during binding of the nucleic acids to the QIAamp Mini Column are depicted in table 2.

Table 2 summarizes the binding conditions in example 2:

|  | Standard | +2 ml IPA | +4 ml IPA | +6 ml IPA | +6 ml IPA | +12 ml IPA |
|---|---|---|---|---|---|---|
| Gu thiocyanate | 2.3 mol/l | 2.08 mol/l | 1.88 mol/l | 1.71 mol/l | 1.71 mol/l | 1.35 mol/l |
| Isopropanol | 19.5% | 30.1% | 36.9% | 42.5% | 42.5% | 54.5% |
| Brij 58 | 10.2% | 9.2% | 8.3% | 7.6% | 7.6% | 6.0% |
| Na SDS | — | — | — | — | 0.13% | 0.10% |
| Total volume | 16.6 ml | 18.6 ml | 20.6 ml | 22.6 ml | 22.6 ml | 28.6 ml |
|  | 4 repl. | 4 repl. | 4 repl. | 4 repl. | 4 repl. [1 ml ATL]* | 4 repl. [1 ml ATL]* |

Figure 2:
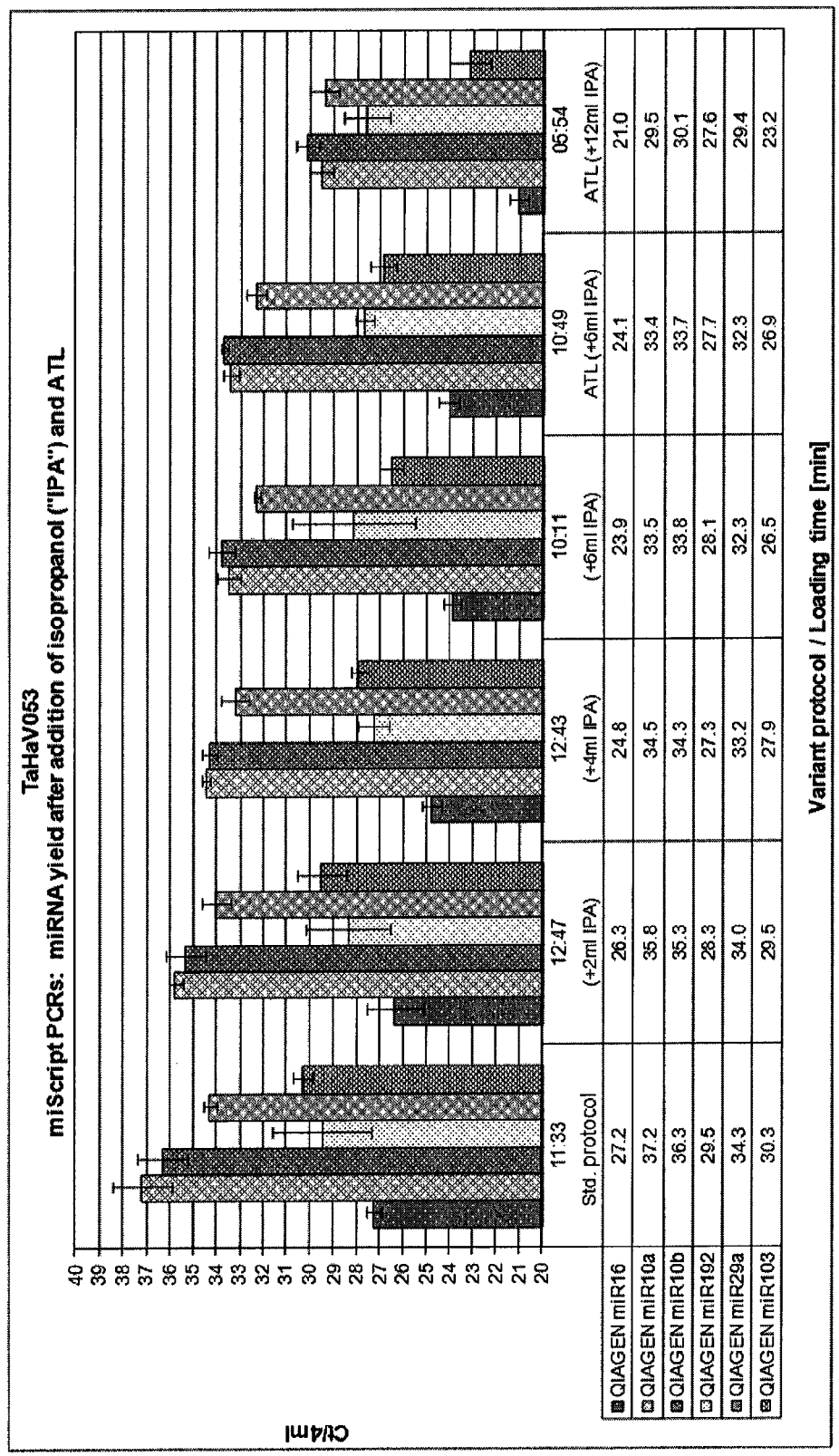

The yield of the isolated miRNAs was determined by means of the miScript real time PCR assay (QIAGEN). 6 different miRNAs were studied. The following was obtained (see also FIG. 2):

As already observed in example 1, the miRNA yield of all miRNAs studied increases with increasing isopropanol concentration during binding; the highest yields are found—based on identical sample volumes—with the addition of 12 ml of isopropanol (approx. 54.5% v/v); here, the yield is approx. 2-8 Ct values higher (4 fold- 250 fold) than in the standard protocol.

There was no case of blocking of the QIAamp columns. Surprisingly, the time for passing the sample over the QIAamp Mini Columns turned out to be shortest (approx. 6 minutes) with 54.5% isopropanol and additionally 0.1% SDS. Employing a combination of high isopropanol concentration and presence of two detergents (in particular the combination of ionic and nonionic) solubilized the sample sufficiently to prevent blocking of the column.

Comparison of the conditions "6 ml of isoprop." and "6 ml of isoprop.+SDS" indicates that the addition of SDS does not cause any significant decrease in the miRNA yield.

III. Example 3

Since it cannot be ruled out on the basis of previous experience that different plasma samples differ in their tendencies to block the QIAamp membranes in vacuum-based nucleic acid extraction, example 2 was repeated using a new plasma pool: in example 3, 6 replicates were studied for each condition. The standard protocol of the QIAamp Circulating Nucleic Acid Kit was compared with variants which previously had achieved the highest miRNA yields. The nucleic acid extraction was carried out according to this protocol:

Disruption of the Sample

400 µl of QIAGEN proteinase K are pipetted into a 50 ml tube, and 4 ml [3 ml] of plasma are added. 3.2 ml of ACL buffer (QIAGEN) are added and also, in the case of the 3 ml samples, 1 ml of buffer ATL; the cap is sealed, followed by mixing by pulse vortexing for 30 s.

The sample is heated to 60° C. and incubated for 30 min. The tube is spun briefly in order to remove drops from the inside of the lid.

Binding

For this, 9 ml of ACB buffer (QIAGEN) were added to the lysate (6 ml of isopropanol in the case of the 4 ml samples, and 6 ml or 12 ml in the case of the 3 ml samples), the lid was closed, followed by thorough mixing by pulse vortexing for 15-30 s. The mixture is incubated on ice for 5 min.

A column (QIAamp Mini Column) may be employed for purification. The column is placed in a VacConnector, and a 20 ml extension tube is placed into the open column. The extension tube must be inserted tightly into the column in order to prevent a loss of the sample. The disrupted sample is introduced into the extension tube of the column and the vacuum pump is switched on. Once the complete lysate has been drawn through the column, the vacuum pump is switched off and the pressure is reduced to 0 mbar. The extension tube is carefully removed.

The remaining steps (washing and elution) were carried out as described in experiment 1. The concentrations of the important components for binding of the nucleic acids are listed in table 3.

Table 3 summarizes the binding conditions in example 3:

|  | Standard | +6 ml IPA | +6 ml IPA | +12 ml IPA |
| --- | --- | --- | --- | --- |
| Gu thiocyanate | 2.3 mol/l | 1.71 mol/l | 1.71 mol/l | 1.35 mol/l |
| Isopropanol | 19.5% | 42.5% | 42.5% | 54.5% |
| Brij 58 | 10.2% | 7.6% | 7.6% | 6.0% |
| Na SDS | — | — | 0.13% | 0.10% |
| Total volume | 14.8 ml | 22.6 ml | 22.6 ml | 28.6 ml |
|  | 4 repl. | 4 repl. | 4 repl. | 4 repl. |
|  |  |  | [1 ml ATL] | [1 ml ATL] |

Figure 3A:
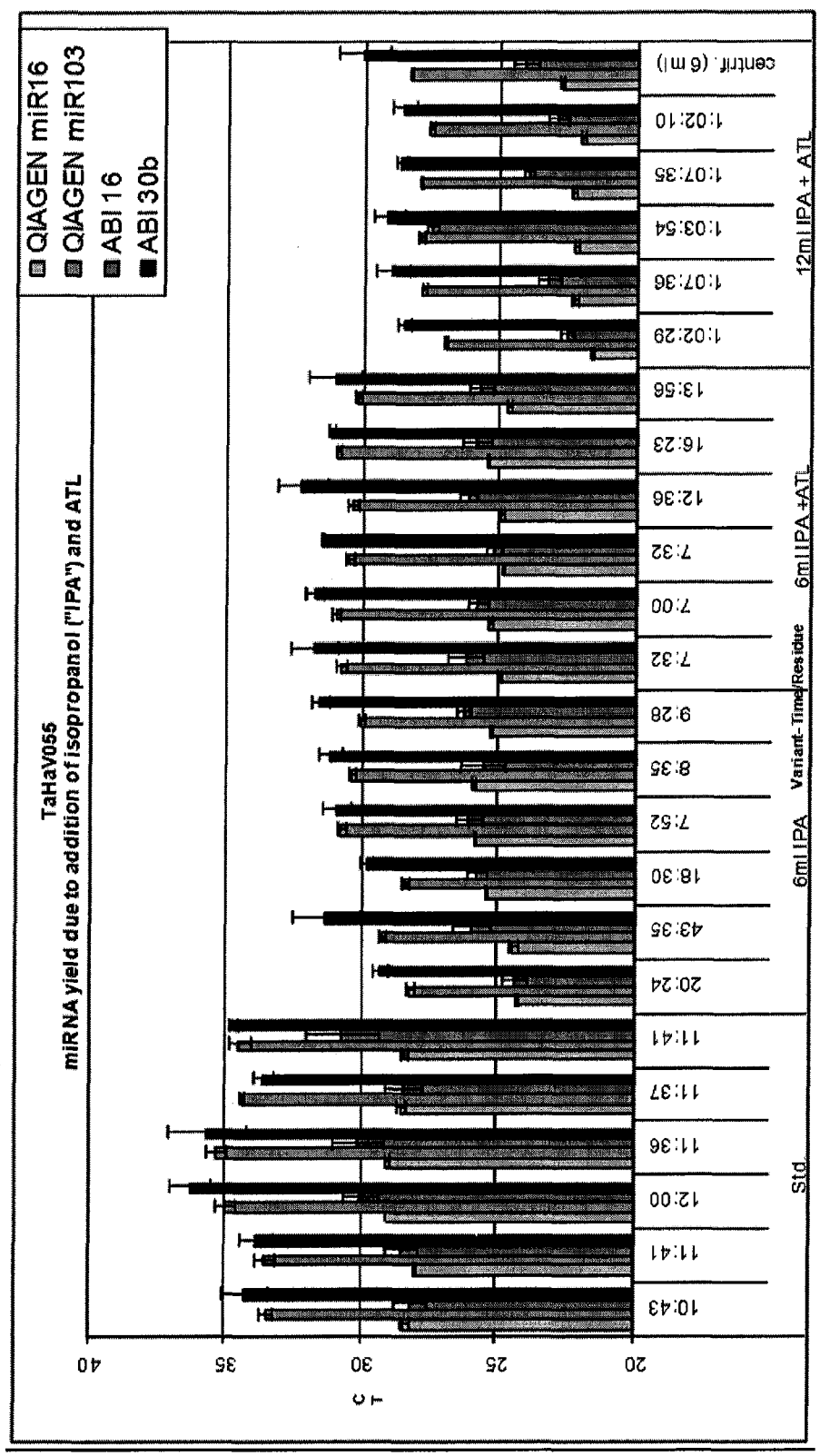
Figure 3B:
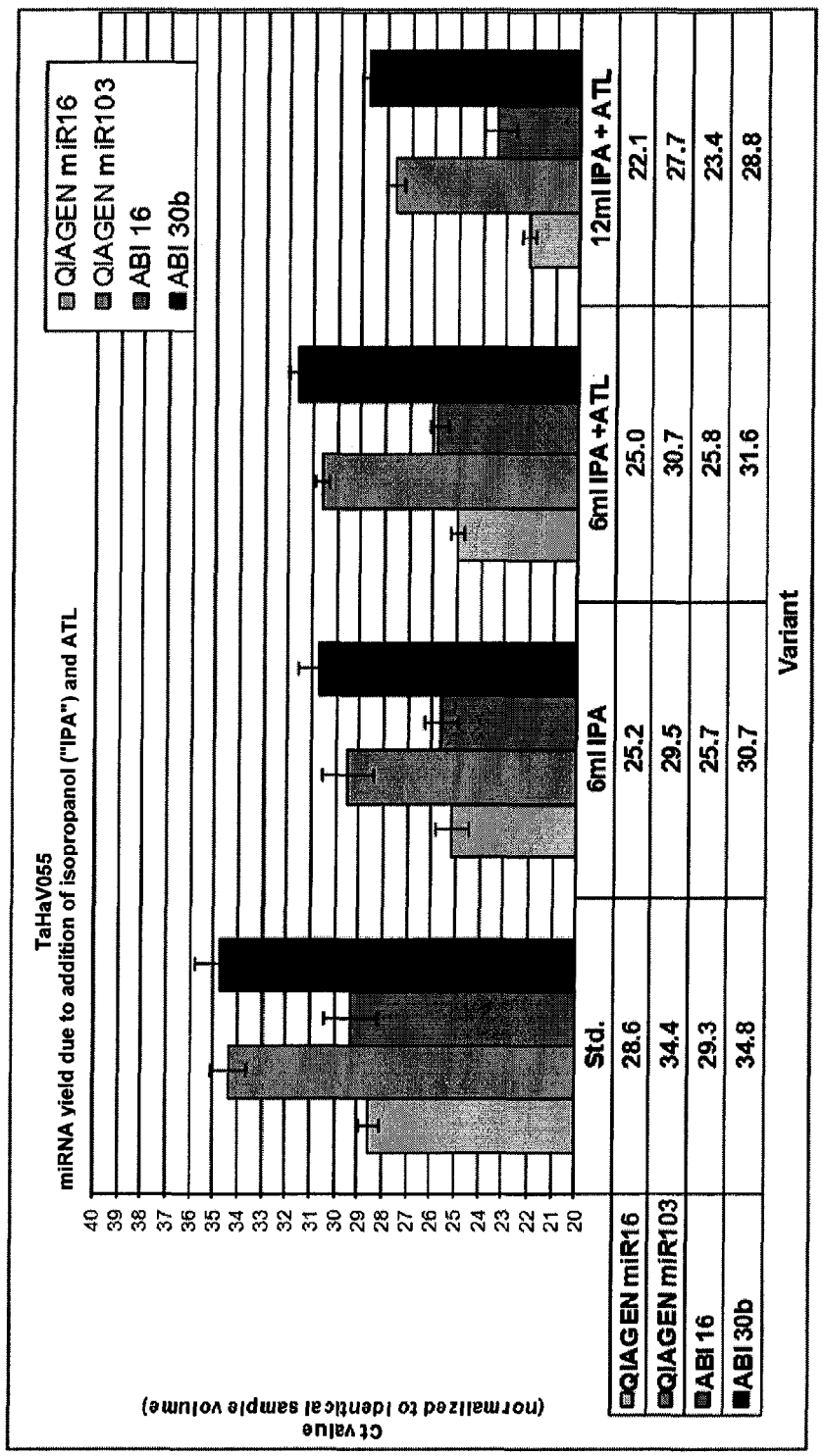

After nucleic acid extraction, the isolated miRNAs were quantified by means of QIAGEN miScript and Applied Biosystems TaqMan assays (see also FIG. 3a/3b).

The following was observed during carrying out of miRNA extraction and miRNA quantification:

For this lot of plasmas, the loading times of the QIAamp columns were generally higher than those observed in experiment 2. As in experiment 2, it also turned out here surprisingly that, with 42.5% isopropanol, the additional presence of SDS during binding results in an accelerated passage of the sample.

With the addition of 12 ml of isopropanol (54.5%), the presence of SDS here enables the complete passage of the samples in almost all replicates within approx. 1 hour.

The miRNA yield with 42.5% isopropanol is approx. 6 Ct values higher than with the standard protocol (60 fold-100 fold); with 54.5% isopropanol, the miRNA yield is still approx. 7-8 fold higher than with 42.5% isopropanol.

The previous experiments demonstrate the advantages of the method of the invention for purifying circulating miRNAs from plasma or serum:

The high isopropanol concentration employed according to the invention is advantageous for the miRNA yield. It is particularly advantageous to use isopropanol rather than ethanol, since the use of ethanol requires higher concentrations (60% (v/v)) to be employed. The latter results in a large increase in the total sample volume in the purification of miRNA from plasma/serum. This should be avoided, if possible, since the sample volume for extraction of free circulating nucleic acids is already preferably high in order to achieve a yield sufficient for diagnostic applications. A very high total volume during nucleic acid extraction is unfavorable for executing the protocol, since the vacuum-based loading of the columns generally takes longer. High volumes are also unfavorable for automated execution of the extraction protocol.

Although the use of a high isopropanol (alcohol) concentration reduces the viscosity of the sample, it also results in unspecific precipitation of components of the sample lysate which may then block the binding membrane in the form of small particles during vacuum processing. A simultaneous use of two detergents (e.g. Brij 58 and SDS) surprisingly reduces the blocking tendency (due to specific better solubilization of isopropanol-induced precipitates) and thus greatly simplifies the performance of the vacuum-based extraction. This is not achieved by using only one detergent (e.g. Brij 58) alone. As a result, the advantageous effect of the high isopropanol concentration on the miRNA yield can be utilized but, at the same time, the disadvantages can be avoided. The protocol illustrated in experiment 3 (1.3-2.5 mol/l Gu thiocyanate, 42-60% isopropanol with 1, preferably 4-6% Brij 58 and 0.1-1.0% SDS) may be employed in particular for miRNA extraction for diagnostic applications.

The invention claimed is:

1. A method of isolating and/or purifying nucleic acids from a nucleic acid-containing starting material, comprising:
    (a) binding the nucleic acids to a nucleic acid-binding support material by contacting the starting material with said nucleic acid-binding support material in the presence of at least one chaotropic compound, at least one ionic detergent, at least one nonionic detergent, and at least one branched and/or unbranched alcohol, wherein the concentration of said alcohol is ≥40% (v/v); and
    (b) optionally eluting the bound nucleic acids from the nucleic acid-binding support material.

2. The method of claim 1, wherein the ionic detergent and the nonionic detergent are surfactants.

3. The method of claim 1, wherein the ionic detergent is used in an amount of at least ≥0.05% (v/v).

4. The method of claim 1, wherein the nonionic detergent is used in an amount of at least ≥1% (w/v).

5. The method of claim 1, wherein
    (a) the ionic detergent and the nonionic detergent are surfactants;
    (b) the ionic detergent is used in an amount of at least ≥0.05% (v/v); and
    (c) the nonionic detergent is used in an amount of at least ≥1% (w/v).

6. The method of claim 1, wherein the ionic detergent is an anionic detergent.

7. The method of claim 6, wherein the ionic detergent is a sulfate or sulfonate of a fatty alcohol.

8. The method of claim 7, wherein the sulfate or sulfonate of a fatty alcohol is sodium dodecyl sulfonate, dodecylbenzenesulfonic acid, N-lauroylsarcosine, or sodium cholate.

9. The method of claim 7, wherein the sulfate or sulfonate of a fatty alcohol is sodium dodecyl sulfate.

10. The method of claim 1, wherein the nonionic detergent is a polyoxyethylene compound.

11. The method of claim 10, wherein the polyoxyethylene compound is a polyoxyethylene alkyl ether.

12. The method of claim 11, wherein the polyoxyethylene alkyl ether is Brij 30, Brij 35, Brij 56, Brij 72, Brij 90, Tween 20, Tween 80, Triton X-100, Triton X-114, Triton X-450, Igepal CA-630, or Nonidet P-40.

13. The method of claim 11, wherein the polyoxyethylene alkyl ether is Brij 58.

14. The method of claim 1, wherein the ionic detergent is an anionic detergent, and the nonionic detergent is a polyoxyethylene compound.

15. The method of claim 1, wherein the anionic detergent is sodium dodecyl sulfate, and the nonionic detergent is Brij 58.

16. The method of claim 1, wherein the nucleic acid-binding support material is a nucleic acid-binding membrane, a nucleic acid-binding filter, or a nucleic acid-binding filter layer, is in a column, or is a bulk of a porous or non-porous support material.

17. The method of claim 1, wherein the chaotropic compound is used in a concentration of at least $\geq 1.0$ mol/l.

18. The method of claim 1, wherein the at least one branched and/or unbranched alcohol comprises isopropanol.

19. The method of claim 1, wherein the alcohol is used in an amount of $\geq 42.5\%$ (v/v).

20. The method of claim 19, wherein the alcohol is used in an amount of $\geq 50\%$ (v/v).

21. The method of claim 1, wherein the nucleic acid-containing starting material is a cell-free sample and/or a sample prepared accordingly.

22. The method of claim 1, wherein the nucleic acid-containing starting material is blood, plasma, or serum.

23. The method of claim 1, wherein the volume of the nucleic acid-containing starting material is $\geq 1$ ml.

24. The method of claim 1, wherein the volume of the nucleic acid-containing starting material is $\geq 3$ ml.

25. The method according to claim 1, wherein the eluting is performed using an elution volume $\geq 10$ to $\leq 200$ μl.

26. The method according to claim 1, wherein the eluting is performed using an elution volume $\geq 10$ to $\leq 150$ μl.

27. The method according to claim 1, wherein the nucleic acids to be isolated comprise short-chain nucleic acids.

28. The method according to claim 1, wherein the nucleic acids to be isolated have one or more of the following characteristics:

(a) they are $\leq 500$ nt, $\leq 400$ nt and/or $\leq 300$ nt and/or $\leq 100$ nt in length;
(b) they are extracellular nucleic acids;
(c) they are non-protein-coding RNAs; and/or
(d) they are RNAi-inducing nucleic acids.

29. The method according to claim 1, wherein the nucleic acids to be isolated comprise miRNAs, and the nucleic acid-containing starting material is a blood sample.

30. The method according to claim 29, wherein the blood sample is blood plasma or serum.

31. The method according to claim 28, wherein
a) the nucleic acids to be isolated are present in the nucleic acid-containing starting material in a mixture with other nucleic acids;
b) after purification and/or isolation, the nucleic acids to be isolated are present in a mixture with other nucleic acids; and/or
c) the nucleic acids, which may be present in a mixture with other nucleic acids after purification/isolation, are further processed, modified, amplified, and/or analyzed after said purification/isolation.

32. The method of claim 1, further comprising:
(c) analyzing the nucleic acids bound to the support material from step (a) or the nucleic acids eluted from the support material from step (b).

33. A kit for isolating and/or purifying nucleic acids from a nucleic acid-containing starting material, comprising:
(a) buffers and/or reagents comprising at least one chaotropic compound, at least one ionic detergent, and at least one nonionic detergent for carrying out a method according to claim 1,
(b) a nucleic acid binding support material, and
(c) instructions for carrying out the method according to claim 1.

34. The kit according to claim 33, wherein the nucleic acids to be isolated and/or purified comprise short-chain nucleic acids.

35. The kit according to claim 33, wherein the nucleic acids to be isolated and/or purified comprise miRNAs, and the nucleic acid-containing starting material is a blood sample.

36. The kit according to claim 33, wherein the nucleic acid binding support material is a nucleic acid-binding membrane, a nucleic acid-binding filter, or a nucleic acid-binding filter layer, is in a column, or is a bulk of a porous or non-porous support material.

* * * * *